United States Patent
Crowder et al.

(10) Patent No.: US 10,488,064 B1
(45) Date of Patent: Nov. 26, 2019

(54) CONTINUOUS AIR MONITOR

(71) Applicants: Nicholas Dwayne Crowder, Edmond, OK (US); Anthony Herron Mills, Oklahoma City, OK (US); Jack Benjamin Scherlag, Oklahoma City, OK (US)

(72) Inventors: Nicholas Dwayne Crowder, Edmond, OK (US); Anthony Herron Mills, Oklahoma City, OK (US); Jack Benjamin Scherlag, Oklahoma City, OK (US)

( * ) Notice: Subject to any disclaimer, the term of this patent is extended or adjusted under 35 U.S.C. 154(b) by 0 days.

(21) Appl. No.: 15/998,053

(22) Filed: Jun. 19, 2018

(51) Int. Cl.
*F24F 11/30* (2018.01)
*F24F 3/16* (2006.01)
*F24F 110/70* (2018.01)
*F24F 110/66* (2018.01)

(52) U.S. Cl.
CPC ............ *F24F 11/30* (2018.01); *F24F 3/1603* (2013.01); *F24F 2110/66* (2018.01); *F24F 2110/70* (2018.01)

(58) Field of Classification Search
CPC ..... F24F 11/30; G08B 21/12; G01N 33/0062; G01N 33/0031
See application file for complete search history.

(56) References Cited

U.S. PATENT DOCUMENTS

| | | | |
|---|---|---|---|
| 2,972,678 A | 2/1961 | Anton | |
| 5,255,556 A | 10/1993 | Lobdell | |
| 5,428,964 A * | 7/1995 | Lobdell | G05D 27/02 62/176.6 |
| 5,468,968 A | 11/1995 | Bailey | |
| 5,914,453 A * | 6/1999 | James | B01D 46/0086 340/577 |
| 6,011,479 A | 1/2000 | Morgan | |
| 7,631,568 B2 | 12/2009 | Kilps | |
| 7,987,695 B2 | 8/2011 | Kilps | |
| 8,813,593 B2 | 8/2014 | Kilps | |
| 9,141,094 B2 | 9/2015 | Pariseau | |
| 9,311,807 B2 | 4/2016 | Schultz | |
| 9,772,281 B2 | 9/2017 | Bertaux | |
| 9,890,969 B2 | 2/2018 | Martin | |
| 10,295,457 B1 * | 5/2019 | Ocheltree | G01N 21/255 |
| 2002/0074000 A1 * | 6/2002 | Benda | A61M 16/06 128/205.22 |
| 2004/0065204 A1 * | 4/2004 | Dietrich | B01D 46/442 96/111 |
| 2004/0158359 A1 * | 8/2004 | Frecska | G05B 15/02 700/276 |
| 2014/0277624 A1 * | 9/2014 | Pariseau | G05B 11/01 700/90 |

(Continued)

FOREIGN PATENT DOCUMENTS

WO    WO-2018070561 A1 *  4/2018

*Primary Examiner* — Ronald D Hartman, Jr.
(74) *Attorney, Agent, or Firm* — Randal Homburg

(57) ABSTRACT

A portable indoor air quality monitor measures the air surrounding the device and displays those qualities on a liquid crystal display with touchscreen capabilities, the monitor providing an internal power supply, fans to circulate air through a housing, and sensors to detect particulate matter, harmful gasses, volatile organic compounds, CO2, temperature, humidity and atmospheric pressure, the device providing a stationary monitor or one worn by a user, especially a first responder.

5 Claims, 5 Drawing Sheets

(56) References Cited

U.S. PATENT DOCUMENTS

| | | | |
|---|---|---|---|
| 2015/0212057 A1* | 7/2015 | Darveau | G01N 33/004 73/31.03 |
| 2017/0023457 A1* | 1/2017 | Hart | G01N 15/06 |
| 2017/0023458 A1* | 1/2017 | Hart | G01N 21/53 |
| 2017/0193788 A1 | 7/2017 | Kim | |
| 2017/0310809 A1* | 10/2017 | Shi | H04M 1/72527 |
| 2018/0082566 A1* | 3/2018 | Semanoukian | G01N 33/0031 |
| 2019/0051135 A1* | 2/2019 | Semanoukian | G01N 33/0031 |

* cited by examiner

CONTINUOUS AIR MONITOR

CROSS REFERENCE TO RELATED APPLICATIONS

None.

I. BACKGROUND OF THE INVENTION

1. Field of Invention

A portable indoor air quality monitor measures the air surrounding the device and displays those qualities on a liquid crystal display with touchscreen capabilities, the monitor providing an internal power supply, fans to circulate air through a housing, and sensors to detect particulate matter, harmful gasses and volatile organic compounds, CO2, temperature, humidity and atmospheric pressure, the device providing a stationary monitor or one worn by a user, especially a first responder.

2. Description of Prior Art

A preliminary review of prior art patents was conducted by the applicant which reveal prior art patents in a similar field or having similar use. However, the prior art inventions do not disclose the same or similar elements as the present portable air quality monitor, nor do they present the material components in a manner contemplated or anticipated in the prior art.

Numerous prior art patents are designed to measure air quality in one or more different capacities using their disclosed components and component configurations. Some provide for a stationary monitor and other provide for sensors worn or carried by a user. Several stationary device which are connected to monitoring and data interpretation devices include U.S. Pat. No. 2,372,678 to Anton (air particle monitor), App. No 2017/0193788 to Kim (air quality notifying device connected to an air quality monitor), U.S. Pat. No. 9,890,969 to Martin (pollution monitor), U.S. Pat. No. 9,311,807 to Schultz (particle counter, pressure sensor connecting to a data bus), U.S. Pat. No. 7,631,568 to Kilps (particle monitor) and U.S. Pat. No. 5,468,968 to Bailey (an air collection filter means having a bar code indicia). These devices are distinguished by the components used to perform the air quality monitoring, the compact nature of the present air quality monitoring device, the limited diversity of the types of items which may be sensed in the prior art, the monitoring components and the ease and manner of programming the device.

Portable devices which monitor certain aspects of air quality include U.S. Pat. No. 9,772,281 to Bertaux (a particle collector apparatus and an optical sensor assembly with an air flow inlet and outlet), U.S. Pat. No. 5,255,556 to Lobdell (a hand-held air quality machine with a particle and gas level categorical display range), U.S. Pat. No. 6,011,479 to Morgan (a radioactive sensing backpack and detection sensor), and U.S. Pat. Nos. 7,987,695 and 8,813,583 to Kilps, and U.S. Pat. No. 9,141,094 to Pariseau. These devices are distinguished from the present portable air quality monitor by the component used to perform the air quality monitoring, the range of air quality monitoring options provided by the device, and the manner of programming of the components utilized to operate the present air quality monitoring device.

II. SUMMARY OF THE INVENTION

Air quality is important to those who require detection of certain air borne matters that can be detected in small particles either prior to reaching a level of harm or prior to entry into an area where air quality can be lethal or toxic. For example, air quality is important to those with allergies to particulate materials and to a homeowner to detect levels of toxic fumes which can be produced within a home including carbon monoxide, high levels of carbon dioxide, combustion gasses from an appliance that has failed or smoke from a small fire prior to becoming larger. Air quality may also involve the detection of volatile and toxic levels of organic compounds. Volatile organic chemicals are those chemicals having a high vapor pressure at ordinary room temperature and while seldom toxic, they can compound long-term health issues. They are found in paints and coatings, cleaning products, refrigerants, and building products and include benzene, methylene chloride, perchloroethylene, MTBE and formaldehyde.

The present air monitoring device is of simple and compact construction and is provided as a stationary monitor, a hand-held device, on a wristband or on a handle for introduction into a room having a potential hazard often encountered by firefighters, hazardous material teams and other first responders. It can be used simply to monitor allergens in a home or to provide a life saving monitor to those encountering hazardous environments prior to introduction into a certain atmosphere.

III. DESCRIPTION OF THE DRAWINGS

The following drawings are submitted with this utility patent application.

IV. DESCRIPTION OF THE PREFERRED EMBODIMENT

Figure 1:
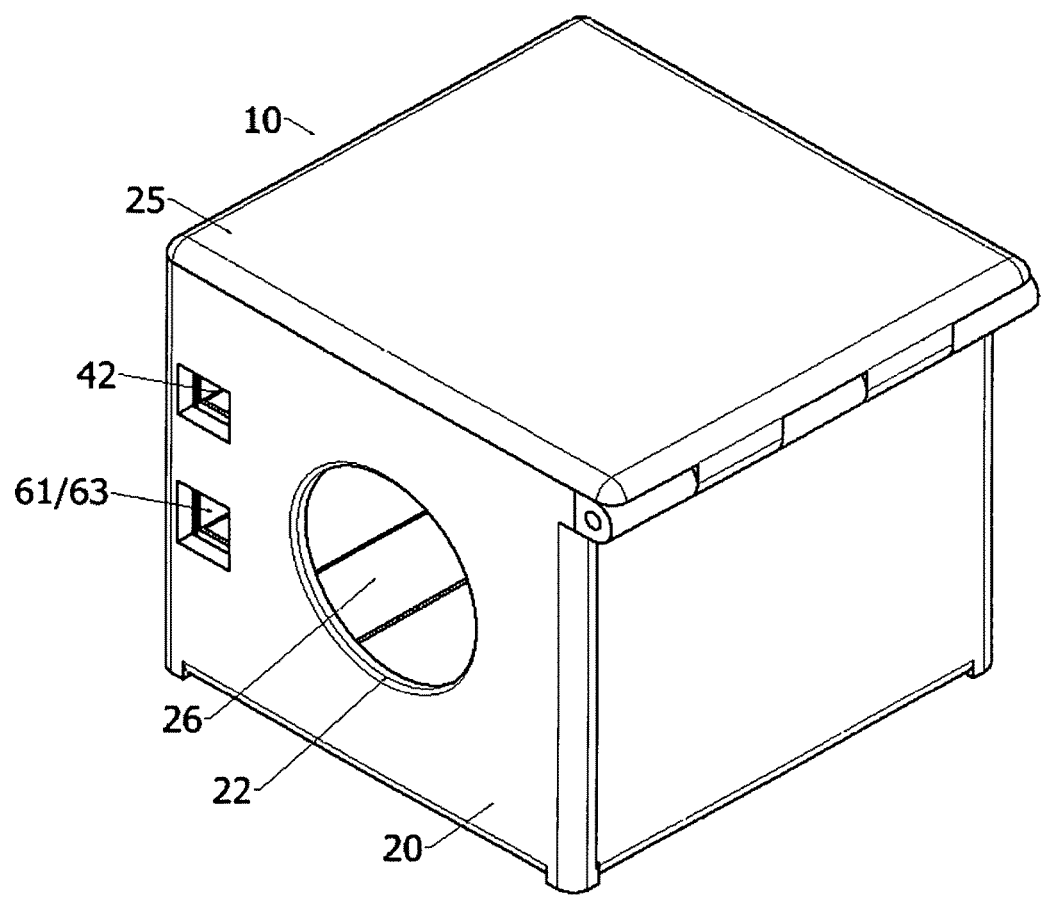
FIG. 1 is a perspective view of the air quality monitoring device.
Figure 2:
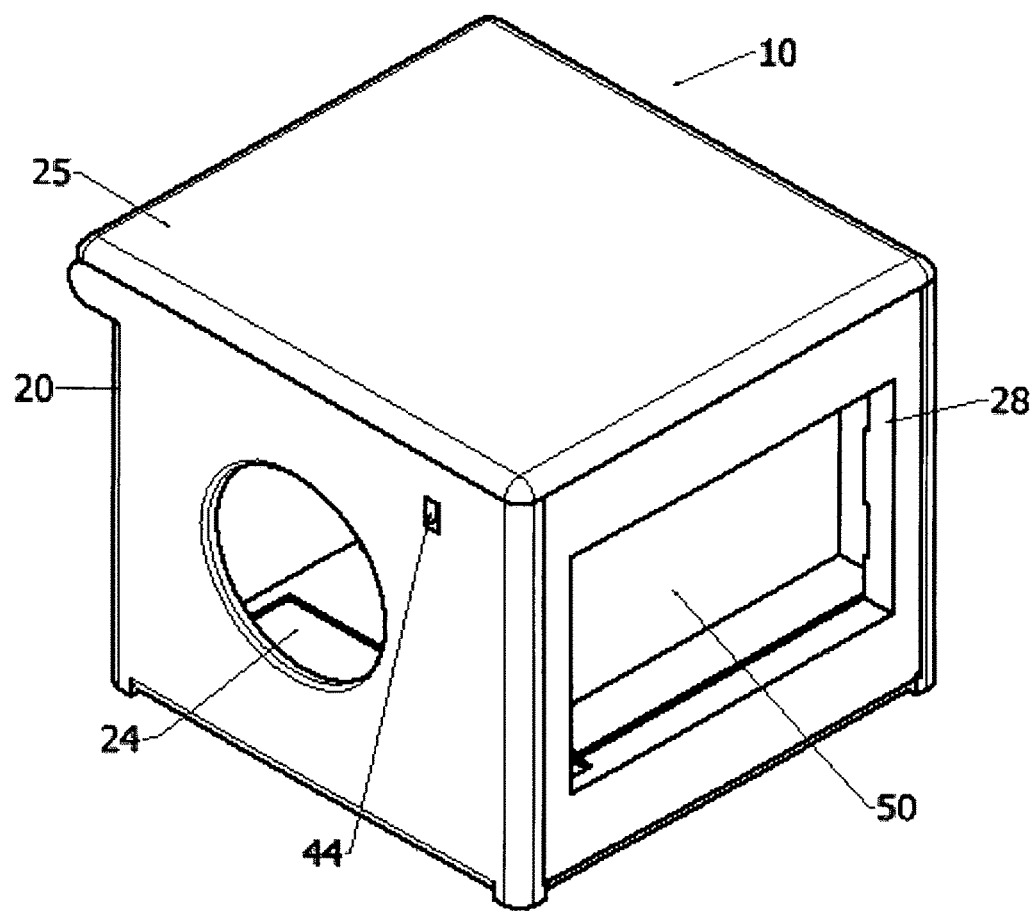
FIG. 2 is an opposite perspective view of the air quality monitoring device.
Figure 3:
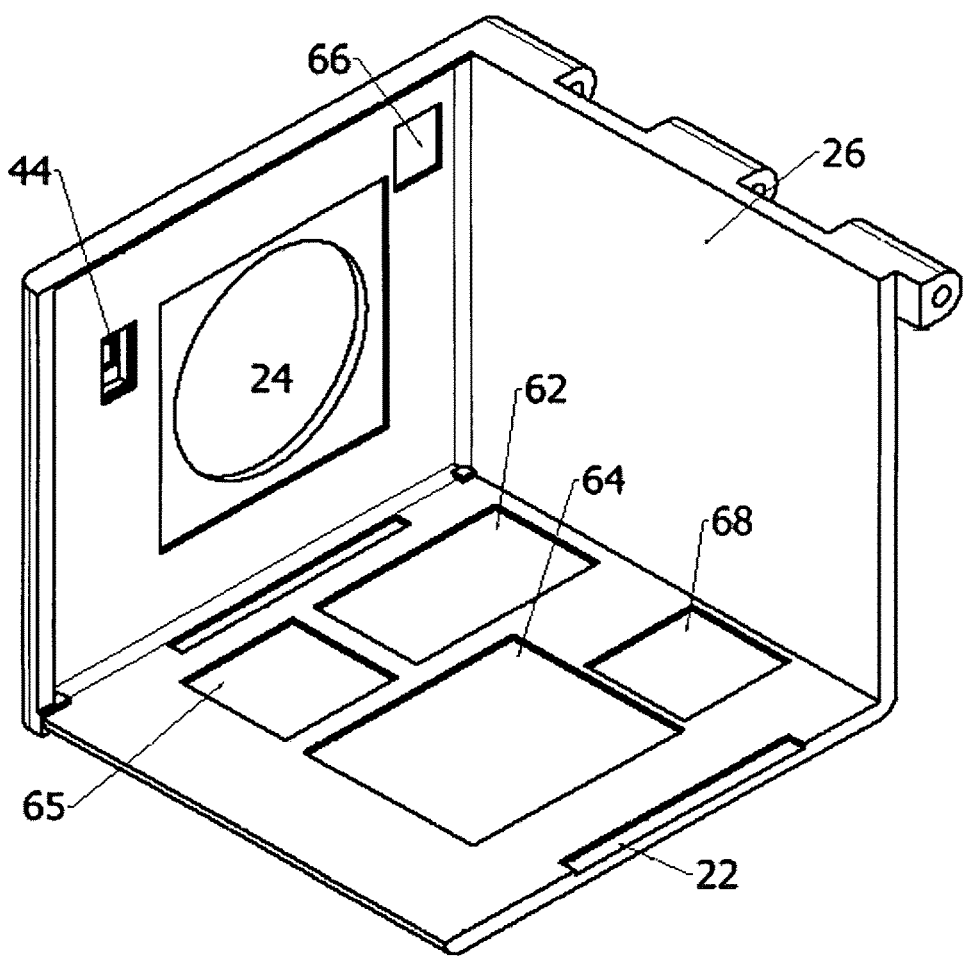
FIG. 3 is an inside view of the air quality monitoring device exposing the inner cavity.
Figure 4:
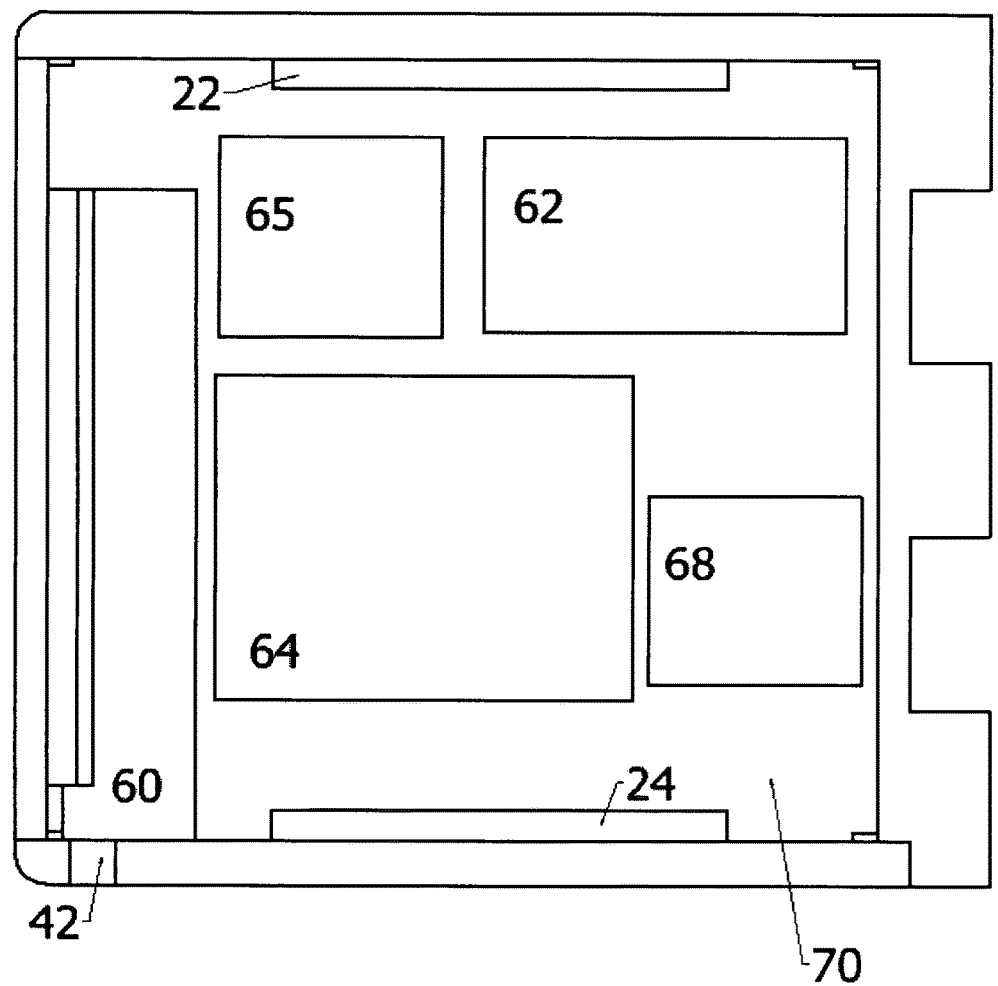
FIG. 4 is an inner view of a side panel including a fan.
Figure 5:
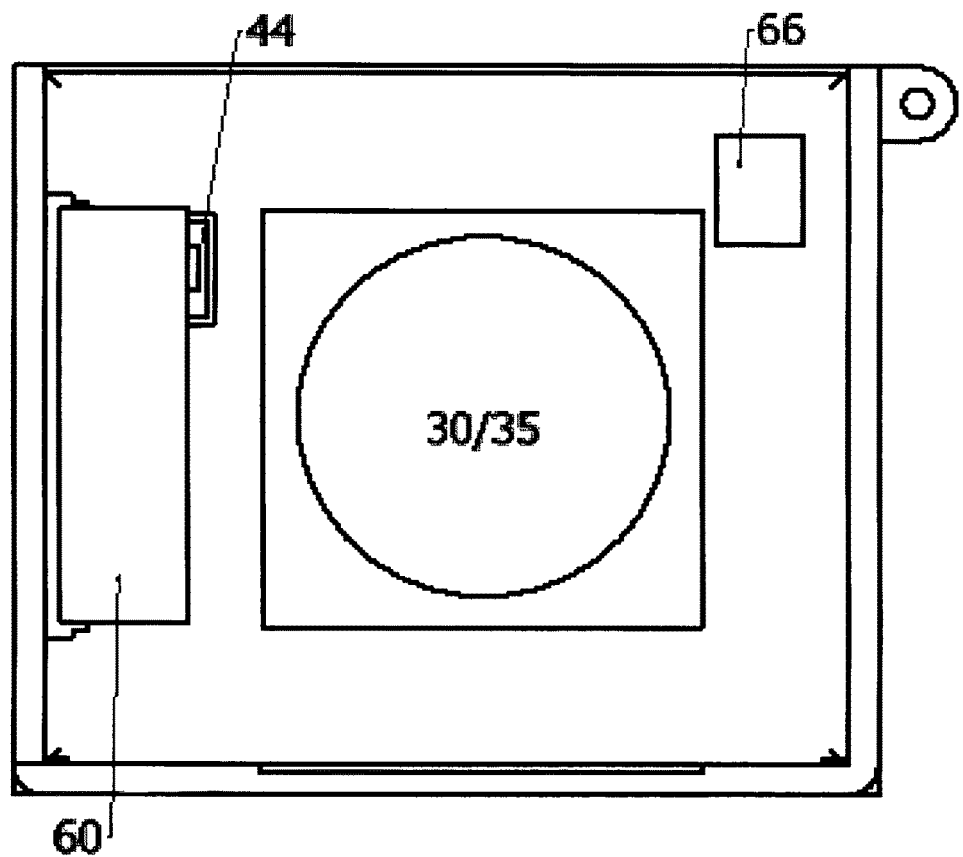
FIG. 5 is a view of the sensing component within the device and the intake and outlet fans.

A compact air quality monitoring device 10, FIGS. 1-5, provides an environmental determination of the air quality in a particular location to measure particulate matter, gasses present in the air, temperature and humidity, air pressure and any presence of a volatile organic compound. The device 10 may be presented as a stationary monitoring station or as a personal portable device small enough to be worn on a wrist or at the end of a probe. The device 10 can measure allergens, toxic or harmful gasses and fumes including carbon monoxide, and volatile organic compounds. It is useful to those who suffer from allergies, for use in home monitoring and also for those first responders who may encounter a toxic or dangerous environment to avoid exposure to harmful elements in a particular environment, such as those assigned to hazardous materials abatement or containment.

The compact air monitoring device 10 provides a container 20 defining at least one intake port 22, one exhaust port 24, an internal cavity 26 and a panel section cutout 28 accepting the installation of a liquid crystal display 50 having touchscreen capability. Each intake port 22 has a first low voltage fan 30 which draws air into the container, with a second low voltage fan 35 eliminating the air inside the container 20 through the outlet port 24. These fans 30, 35, continuously circulate environmental air through the container 20 providing the continuous monitoring capability of the device 10.

Within the internal cavity 26 is an internal low voltage power supply 40, not shown, preferably a 12 volt 1800 mAh lithium ion battery which can be recharged as the battery may require. The battery operates all the electrical components disclosed as part of the device 10. The electronic components of the device include a first microcontroller 60, a second microcontroller 62, a particulate matter sensor 64, a gas and volatile organic compound sensor 65, a temperature/humidity sensor 66, and at atmospheric pressure device 68. The ideal and best mode sensors and microcontrollers 60, 62, are disclosed below.

The first microcontroller 60 is best indicated by an Adafruit 5vPro Trinket (Trinket) or substantial equivalent, if any. The second microcontroller 62 is best indicated as a standard Arduino Uno (Uno) or substantial equivalent, if any. The particulate matter sensor 64 is identified optimally as having a serial number of SEN0177 and is powered by a 5 volt signal. The particulate matter sensor 64 must measure PM 1.0, PM 2.5 and PM 10. An adapter is required with this sensor and converts 3.3 volt logic to 5 volt logic, and is connected to the second microcontroller 62 (Uno) using software serial to send data to the second microcontroller 62. This particulate matter sensor 64 can be categorically referenced as a laser dust particulate matter detector, which is a generic term used for this type sensor by those skilled in the art, although the particular particulate matter sensor 64 SEN0177, disclosed as optimal is that sensor known to operate without issue using the other optimal components within the device 10.

The gas and volatile organic compound sensor 65 is identified optimally as an Adafruit CCS811 or substantial equivalent, if any. The gas and volatile organic compound sensor 65 must be capable of sensing general trends in the circulated air to detect CO2 in parts per million and volatile organic compounds in parts per billion. The gas and volatile organic compound sensor 65 communicates with the first microcontroller 60 (Trinket) using 12C communication. A primary temperature/humidity sensor 66 is identified optimally as a DHT11, or substantial equivalent, if any, which is powered by a 5 volt signal, requiring a resistor within a data wire, which connects the DHT11, or its substantial equivalent, if any, to the first microcontroller 60 (Trinket) in the analog section. Atmospheric pressure sensor 68 reading is optimally provided by an Adafruit BME680 or substantial equivalent, if any, measuring air pressure in pascals, with temperature measured in Celsius, humidity measured in relative percent and gas in Kohms. This atmospheric pressure sensor 68 is connected to the first microcontroller 60 (Trinket) via SPI communication. The microcontrollers 60, 62, communicate and formulate the data reading which are digitally displayed on the liquid crystal screen 50.

One or more PCB boards 70 are utilized to provide all the wiring used for the microcontrollers 60, 62, power supply 40 and multiple sensors. A power jack 42 in each microcontroller 60, 62 is present to connect to the internal power supply or, alternatively, the power jack 42 from the first microcontroller 60 may extend outside the container 20 for attachment to an external 12 volt power connection. There is also a respective coding port 61, 63, on each microcontroller 60, 62, in order to upload new data an to update old code, which may extend outside the container 20 for external connection to a programming device for code update and downloading without intrusion into the container 20. The container 20 should also provide an access panel 25 to access the electronic components for periodic update, initial programming and reprogramming. A power switch 44 should also be installed in the container 20 which turn the monitoring device 10 on and off. The low voltage power supply 40 may be incorporated into either or both of the two microcontrollers 60, 62, with the power jack 42 having an outside presentation on the monitoring device 10.

The device 10 repeatedly cycles air through the device, with cycled readings conducted several times per second as the air flows through the internal cavity 26. During a cycle, the sensors connected to the first microcontroller 60 (Trinket) send the appropriate values to the first microcontrollers 60 (Trinket). The program within the first microcontroller 60 takes the data and organizes it prior to sending it to the second microcontroller 62 (Uno). Serial communication is used to transfer bytes between the first microcontroller 60 and second microcontroller 62, with the second microcontroller 62 first reading the particulate matter sensor 64, then reading the values sent by the first microcontroller 60 (Trinket). After two or three cycles, the data is then organized and aligned on the LCD display panel 50.

Each microcontroller 60, 62, has virtual unlimited programming capacity, and the sensors allow the compact air quality monitoring device to be programmed to read and detect particles of several plants or air contaminants as well as a variety of harmful chemicals. As previously indicated, it can detect pollen particles which are too small to see without the use of the particulate matter sensor 64, and therefore useful as a stationary monitor. For those who may be exposed to hazardous chemical vapors or the presence of health threatening biologicals, the device can be useful as either fitted upon a probe or elongated handle to be inserted into an area prior to entry or worn on the wrist or body of a first responder in order to monitor and assess the environment for safety risks often encountered, including the presence of gasses in drug labs or even the detection of chemical and biological warfare devices.

While the compact air quality monitoring device 10 has been particularly shown and described with reference to a preferred embodiment thereof, it will be understood by those skilled in the art that changes in form and detail may be made therein without departing from the spirit and scope of the invention.

What is claimed is:

1. A compact air quality monitoring device providing an environmental determination of the air quality in a particular location to measure particulate matter, gasses present in the air, temperature and humidity, air pressure and a presence of a volatile organic compound, said compact air monitoring device comprising:
    a container defining at least one intake port, one exhaust port, an internal cavity and a panel section cutout accepting the installation of a liquid crystal display having touchscreen capability;
    a first low voltage fan which draws air into said container through said at least one intake port;
    a second low voltage fan eliminating air inside said container through said at least one outlet port, said first and second low voltage fans continuously circulating environmental air through said container providing continuous monitoring capability of said compact air quality monitoring device;
    a power supply;
    a first microcontroller, a second microcontroller, a particulate matter sensor, a gas and volatile organic compound sensor, a temperature/humidity sensor, and at atmospheric pressure device operated by said internal low voltage power supply respectively monitoring said air within said container to provide information displayed upon said liquid crystal display information regarding said air.

2. The compact air quality monitoring device of claim 1, further comprising:
said power supply is a power jack or an internal 12 volt 1800 mAh lithium ion battery which can be recharged as required;
said first microcontroller is an Adafruit 5vPro Trinket (Trinket) or substantial equivalent;
said second microcontroller is a standard Arduino Uno (Uno) or substantial equivalent;
said particulate matter sensor is a serial number of SEN0177 powered by a 5 volt signal, said particulate matter sensor having capacity to measure PM 1.0, PM 2.5 and PM 10 with an adapter required to convert 3.3 volt logic to 5 volt logic, and connected to said second microcontroller (Uno) using software to send data to said second microcontroller;
said gas and volatile organic compound sensor is an Adafruit CCS811 or substantial equivalent, capable of sensing general trends in the circulated air to detect CO2 in parts per million and volatile organic compounds in parts per billion, said gas and volatile organic compound sensor further communicating with said first microcontroller (Trinket) using 12C communication;
said primary temperature/humidity sensor is a DHT11, or substantial equivalent, which is powered by a 5 volt signal, requiring a resistor within a data wire, connecting to said first microcontroller (Trinket);
an atmospheric pressure sensor an Adafruit BME680 or substantial equivalent measuring air pressure in pascals, with temperature measured in Celsius, humidity measured in relative percent and gas in Kohms, said atmospheric pressure sensor connected to said first microcontroller (Trinket) via SPI communication, wherein said first and second microcontrollers (Trinket and Uno) communicate and formulate data readings which are digitally displayed on said liquid crystal screen; and
one or more PCB boards to provide all the wiring, integration and connection for said microcontrollers, power supply and sensors.

3. The compact air quality monitoring device of claim 1, further comprising:
a power jack in each microcontroller is present to connect to the internal power supply or, alternatively, each said power jack from said microcontrollers extending outside said container for attachment to an external 12 volt power connection;
a respective coding port on each microcontroller to upload new data and to update old code, extending outside said container for external connection to a programming device for code update and downloading without intrusion into the container;
an access panel in said container to access electronic components for periodic update, initial programming and reprogramming; and
a power switch installed in said container to turn said compact air quality monitoring device on and off.

4. The compact air quality monitoring device of claim 1, wherein said compact air quality monitoring device repeatedly cycles air through said container, with cycled readings conducted several times per second as the air flows through said internal cavity and wherein during each cycle, said sensors connected to the first microcontroller (Trinket) send data signals to said first microcontrollers (Trinket) which further takes said data signals and organizes them prior to transfer to said second microcontroller (Uno) using serial communication, after which, after two or three cycles, said data signals are then organized and aligned on said LCD display panel.

5. The compact air quality monitoring device of claim 1, further comprising each said microcontroller includes an internal, rechargeable power supply which is presented as a 12 volt 1800 mAh lithium ion battery which can be recharged as required with a power jack in each said microcontroller presented to connect to an external 12 volt power connection for recharging.

* * * * *